United States Patent
Kissinger et al.

(10) Patent No.: US 6,703,530 B2
(45) Date of Patent: Mar. 9, 2004

(54) CHEMICAL REACTOR SYSTEM AND PROCESS

(75) Inventors: Gaylord Michael Kissinger, Evansville, IN (US); Allen Wai-Yee Ko, Evansville, IN (US); Michael D. Szillat, Evansville, IN (US); Brian T. Carvill, Evansville, IN (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/683,898

(22) Filed: Feb. 28, 2002

(65) Prior Publication Data

US 2003/0166976 A1 Sep. 4, 2003

(51) Int. Cl.[7] .............................................. C07C 39/16
(52) U.S. Cl. .................................................... 568/728
(58) Field of Search ........................................ 568/728

(56) References Cited

U.S. PATENT DOCUMENTS

| | | | |
|---|---|---|---|
| 3,029,294 A | 4/1962 | Keeble | |
| 3,454,653 A | 7/1969 | Larson | 260/621 |
| 3,914,351 A | 10/1975 | McKeown | 261/98 |
| 3,957,931 A | 5/1976 | Ellis | 261/98 |
| 4,041,113 A | 8/1977 | McKeown | 261/98 |
| 4,086,307 A | 4/1978 | Glaspie | 261/97 |
| 4,122,011 A | 10/1978 | Strigle, Jr. | 210/150 |
| 4,167,456 A | 9/1979 | Murtha | |
| 4,348,542 A | 9/1982 | Serini | |
| 4,369,293 A | 1/1983 | Heydenreich | |
| 4,387,251 A | 6/1983 | Meyer | |
| 4,912,263 A | 3/1990 | Rudolph | |
| 4,931,594 A | 6/1990 | Knebel | |
| 4,996,373 A | 2/1991 | Bottenbruch | |
| 5,105,027 A | 4/1992 | Desmurs | |
| 5,185,475 A | 2/1993 | Kissinger | 568/748 |
| 5,233,096 A | 8/1993 | Lundquist | 568/727 |
| 5,244,929 A | 9/1993 | Gottlieb et al. | 521/29 |
| 5,245,088 A | 9/1993 | Fimuro | |
| 5,248,839 A | 9/1993 | Iimuro | |
| 5,269,887 A | 12/1993 | Jakob | |
| 5,300,700 A | 4/1994 | Malamet | |
| 5,302,774 A | 4/1994 | Berg | |
| 5,315,042 A | 5/1994 | Cipullo | 568/727 |
| 5,371,304 A | 12/1994 | Asaoka et al. | 568/724 |
| 5,395,857 A | 3/1995 | Berg et al. | 521/33 |
| 5,414,154 A | 5/1995 | Jenczewski et al. | 568/754 |
| 5,502,259 A | 3/1996 | Zakoshansky et al. | 568/754 |
| 5,518,699 A | 5/1996 | Kashnitz et al. | 422/211 |
| 5,545,764 A | 8/1996 | Berg | |
| 5,629,457 A | 5/1997 | Zhang | |
| 5,696,295 A | 12/1997 | Wulff | |
| 5,698,600 A | 12/1997 | Wulff | |
| 5,759,942 A | 6/1998 | Tan | |
| 5,780,688 A | 7/1998 | Hoffmann et al. | 568/697 |
| 5,785,823 A | 7/1998 | Meurer | |
| 5,789,628 A | 8/1998 | Auer et al. | 568/727 |
| 6,008,315 A | 12/1999 | Kimura et al. | 528/176 |
| 6,013,845 A | 1/2000 | Allan et al. | 568/728 |
| 6,211,417 B1 | 4/2001 | Fengler | |
| 6,288,284 B1 | 9/2001 | Eek | |
| 6,294,702 B1 | 9/2001 | Fennhof | |
| 6,307,111 B1 | 10/2001 | Fennhoff | |
| 6,329,556 B1 | 12/2001 | Sakura | |
| 6,384,288 B1 | 5/2002 | Kuhling | |
| 6,414,198 B1 | 7/2002 | Lanze | |
| 6,414,199 B1 | 7/2002 | Saruwatari | |
| 6,429,343 B1 | 8/2002 | Iwahara | |
| 6,486,363 B1 | 11/2002 | Berg | |
| 2003/0013925 A1 | 1/2003 | Iwahara | |

FOREIGN PATENT DOCUMENTS

| | | |
|---|---|---|
| EP | 0 023 572 B1 | 4/1984 |
| EP | 0 045 959 B1 | 4/1984 |
| EP | 0 109033 A2 | 5/1984 |
| EP | 0 113 036 A2 | 7/1984 |
| EP | 0 123 210 A2 | 10/1984 |
| EP | 0 049 411 B1 | 3/1986 |
| EP | 0 144 735 B1 | 11/1987 |
| EP | 0 110242 B1 | 5/1988 |
| EP | 0 332 878 A1 | 9/1989 |
| EP | 0 249 102 B1 | 11/1989 |
| EP | 0 210 366 B1 | 1/1990 |
| EP | 0 358 992 A2 | 3/1990 |
| EP | 0 268 318 B1 | 11/1990 |
| EP | 0 265 792 B1 | 3/1991 |
| EP | 0 229 357 B1 | 4/1991 |
| EP | 0 426 846 A1 | 5/1991 |
| EP | 0 324 080 B1 | 2/1992 |
| EP | 0 329 075 B1 | 2/1992 |
| EP | 0 319 327 B1 | 4/1992 |
| EP | 0 290 179 B1 | 1/1993 |
| EP | 0 313 165 B1 | 1/1993 |
| EP | 0 373 730 B1 | 3/1993 |
| EP | 0 330 146 B1 | 5/1993 |
| EP | 0 332 203 B1 | 5/1993 |
| EP | 0 343 349 B1 | 5/1993 |
| EP | 0 310 925 B1 | 6/1993 |
| EP | 0 373 728 B1 | 6/1993 |
| EP | 0 343 382 B1 | 7/1993 |

(List continued on next page.)

OTHER PUBLICATIONS

WO 01/37992 A1 PCT May. 31, 2001 Abstract Only.

*Primary Examiner*—Michael L. Shippen

(57) ABSTRACT

A method for producing bisphenol includes introducing a phenol and a ketone into a fixed, supported catalytic bed reactor system in a downflow mode, reacting the phenol and the ketone to form a reaction mixture, and recovering the bisphenol isomer from the reaction mixture. The preferred bisphenol isomer is bisphenol A, or p,p'-bisphenol A, produced from the reaction of phenol and acetone. The reactor for producing the bisphenol A from the reaction of phenol and acetone includes an ion exchange resin catalyst disposed in a bed and packing randomly distributed throughout the ion exchange resin catalyst to improve heat transfer efficiency and reduce compression of the catalyst bed.

14 Claims, 3 Drawing Sheets

FOREIGN PATENT DOCUMENTS

| | | |
|---|---|---|
| EP | 0 386 845 B1 | 8/1993 |
| EP | 0 558 214 A1 | 9/1993 |
| EP | 0 559 372 B1 | 9/1993 |
| EP | 0 486 277 B1 | 11/1993 |
| EP | 0 417 407 B1 | 5/1994 |
| EP | 0 616 993 A1 | 9/1994 |
| EP | 0 475 893 B1 | 12/1994 |
| EP | 0 442 122 B1 | 3/1995 |
| EP | 0 486 109 B1 | 3/1995 |
| EP | 0 469 689 B1 | 9/1995 |
| EP | 0 552 518 B1 | 9/1995 |
| EP | 0 342 758 B1 | 10/1995 |
| EP | 0 567 857 B1 | 11/1995 |
| EP | 0 526 964 B1 | 10/1996 |
| EP | 0 643 032 B1 | 2/1997 |
| EP | 0 765 685 A2 | 4/1997 |
| EP | 0 788 839 A1 | 8/1997 |
| EP | 0 620 041 B1 | 9/1997 |
| EP | 0 671 376 B1 | 9/1997 |
| EP | 0 812 815 A2 | 12/1997 |
| EP | 0 812 815 A3 | 12/1997 |
| EP | 0 630 878 B1 | 3/1998 |
| EP | 0 829 464 A3 | 3/1998 |
| EP | 0 829 464 A2 | 3/1998 |
| EP | 0 675 097 B1 | 4/1998 |
| EP | 0 682 004 B1 | 7/1998 |
| EP | 0 680 943 B1 | 8/1998 |
| EP | 0 718 267 B1 | 12/1998 |
| EP | 0 718 268 B1 | 12/1998 |
| EP | 0 694 517 B1 | 1/1999 |
| EP | 0 720 976 B1 | 1/1999 |
| EP | 0 676 237 B1 | 3/1999 |
| EP | 0 926 118 A1 | 6/1999 |
| EP | 0 680 786 B1 | 7/1999 |
| EP | 0 779 590 B1 | 10/2001 |
| EP | 1 142 640 A1 | 10/2001 |
| EP | 1 149 816 A1 | 10/2001 |
| EP | 0 785 181 B1 | 12/2001 |
| EP | 0 918 046 B1 | 4/2002 |
| WO | WO 80/00150 | 2/1980 |
| WO | WO 92/00943 | 1/1992 |
| WO | WO 92/09550 | 6/1992 |
| WO | WO 94/19302 | 9/1994 |
| WO | WO 94/24079 | 10/1994 |
| WO | WO 96/06819 | 3/1996 |
| WO | WO 97/08122 | 3/1997 |
| WO | WO 97/22573 | 6/1997 |
| WO | WO 97/34688 | 9/1997 |
| WO | WO 99/33777 | 7/1999 |
| WO | WO99/48854 | 9/1999 |
| WO | WO 00/15589 | 3/2000 |
| WO | WO00/23408 | 4/2000 |
| WO | WO 00/35847 | 6/2000 |
| WO | WO 00/50372 | 8/2000 |
| WO | WO 00/53315 | 9/2000 |
| WO | WO 00/59853 | 10/2000 |
| WO | WO00/67895 | 11/2000 |
| WO | WO 01/34544 A1 | 5/2001 |
| WO | WO 01/36358 A1 | 5/2001 |
| WO | WO 01/37992 A1 | 5/2001 |
| WO | WO01/40155 A1 | 6/2001 |
| WO | WO 01/46105 A1 | 6/2001 |
| WO | WO 01/72677 A1 | 10/2001 |
| WO | WO 01/74488 A1 | 10/2001 |
| WO | WO 01/74489 A1 | 10/2001 |

CHEMICAL REACTOR SYSTEM AND PROCESS

BACKGROUND OF INVENTION

This disclosure relates generally to a chemical reactor system employing a rigid packing material that provides selected support to a packed catalyst bed. More particularly, the disclosure relates to the production of bisphenols in a downflow mode through a bed of cross-linked ion exchange resin catalyst interspersed with and supported by a randomly distributed, substantially inert packing material.

Ensuring that reacting species achieve optimal physical contact is a difficult challenge in chemical reactor design. If done improperly, numerous undesired byproducts and an abundance of unreacted reactants can seriously impact the economics of the system. The reactor type, reactant and production diffusion, pressure effects, and other factors must all be considered in selecting or fabricating a reactor system best suited for use in a given reaction.

Reactor residence time and reaction conditions such as temperature impact the percentage of atomic or molecular collisions and thus affect yield, throughput, and selectivity. Pressure becomes important if the differential pressure compresses and deforms the spherical catalyst beads causing a reduction in liquid throughput as a result of pressure drop limitations.

In reactors having packed beds, fluid flow properties oftentimes suffer significant disruption of flow, or "channeling". This is especially evident in upflow mode. Channeling is a condition that may be caused by an inadequate pressure differential over the height of the bed through which the fluid flows, and typically results from settling of the bed components coupled with too little differential pressure applied over the height of the bed. If the bed components include a catalyst or a similar particulate treatment agent that allows for the random flow of fluid through the bed, portions of the bed may be short-circuited and not contacted by the fluid in a uniform and consistent manner. Such a condition can lead to the incomplete treatment or incomplete chemical reaction of the charged reactants. This, in turn, can result in the premature disposal of the catalyst or treatment particles, which translates into loss of part of the value of the catalyst.

The amount of channeling that occurs can be related to reactor geometry and type; fluid dynamics of the reactants, intermediates and products produced in the reactor; and other factors. In some processes optimizing the production of products by adjusting these parameters is easily understood and straightforward. In others, the relationships are not quite as clear. The employment of carefully selected catalysts complicates reactor design and reaction control. For example, U.S. Pat. No. 5,395,857 proposes that in the production of bisphenol A (BPA) in a downflow reactor, the degree of crosslinking of certain ion exchange resin catalysts directly affects the physical performance of the process as well as the reactivity and selectivity of the reaction. This patent found that the hydraulic impact attributable to catalyst particle shape and the compression of a catalyst bed due to pressure can be lessened by using a two-layer catalyst in which one of the layers exhibits a 2% or lower degree of crosslinking. The process is directed to increasing the volume and time yield of fixed bed reactors. This design permits a higher throughput and production due to an overall greater bed rigidity, while gaining the important aspects of the lower 2% crosslinked catalyst in the top portion where the bulk of the conversion of the reactants occur. The combined catalyst bed proposed in U.S. Pat. No. 5,395,857 has greater selectivity and activity than others and would be desirable because resin-based catalysts with greater degrees of crosslinking are more subject to deactivation and thus become inactive more readily. For example, in downflow processes the potential for catalyst bed collapse at high flow rates because of the low degree of crosslinking and the effects that this has on the physical properties of the catalyst must be considered and ways of reducing or eliminating this problem would be advantageous.

In addition, because of channeling and the resultant inefficient contact of the reactants with the catalyst, the operation of packed bed reactors is often significantly hindered. In particular, operations in which significant amounts of channeling occur generally result in low product yield, premature replacement of catalyst beds, and inefficient use of the reactants. This results not only in the cost of new catalyst, but also loss of production during outages, the logistical costs of replacement, used catalyst disposal costs, and recovery and recycling of the reactants. Furthermore, a significant financial burden may be realized as a result of costs associated with efforts to improve catalyst technology. Such costs involve the development of alternate reactor geometries but do not address the problem of existing reactors which have less favorable geometric features.

With respect to the downflow configuration of reactants into a reactor having a fixed catalyst bed, depending upon selection of the catalyst, the compression due to pressure within the catalyst bed can result in a significant hindrance of the physical performance of the process, as well as the reactivity and selectivity of the reaction. Attempts have been made to utilize a catalyst having a more robust architecture in order to minimize the compression of catalyst particles. This often, however, results in catalysts which are less active, are less selective, or have a shorter lifetime.

Furthermore, there is a direct relationship between the rigidity of catalyst particles and the expected active lifetime of those particles. Particles having an open effective pore structure, which is characteristic of catalysts having a small degree of crosslinking, and catalysts having a less rigid structure, can be expected to result in the reduction or elimination of fouling of the resin catalyst with tar-like molecules that block access to the active acid sites. On the other hand, particles having a less open effective pore structure and greater rigidity would resist compression better, but they may lead to the premature deactivation of the catalyst resin through fouling, thereby resulting in increased costs.

While existing reactor geometries and catalysts are suitable for their intended purposes, there still remains a need for improvements, particularly regarding the effectiveness of the reaction and the catalyst itself in a downflow reactor. Therefore, a need exists for a reactor system that allows the full potential of the selected resin catalyst to be exploited for example, by mitigating associated hydraulic limitations.

SUMMARY OF INVENTION

A method, a reactor and a system utilizing a packed ion exchange resin catalyst bed supported by discrete interspersed inert elements is disclosed herein.

In a first embodiment, a method for producing a bisphenol is disclosed comprising introducing a phenol and a ketone into a reactor in a downflow mode. The reactor comprising an ion exchange resin catalyst bed, and packing randomly distributed in the bed; reacting the phenol and the ketone to form a reaction mixture; and recovering the bisphenol from the mixture.

In a second embodiment, a method for producing a bisphenol is disclosed comprising introducing a phenol and a ketone into a reactor system in a downflow mode, the reactor system comprising a downflow chemical reactor, and a fixed bed ion exchange resin catalyst charged in the reactor wherein the resin catalyst is a sulfonated aromatic resin having a degree of crosslinking no greater than about 2% by weight based on the resin catalyst; reacting the ketone and the phenol in the reactor to form a reaction mixture containing the bisphenol; and recovering the bisphenol from the mixture.

In a third embodiment, a reactor is disclosed for producing bisphenol A from the reaction of phenol and acetone introduced therein in a downflow mode, the reactor comprising a reactor vessel, an ion exchange resin catalyst bed in the vessel, and packing randomly distributed throughout the ion exchange resin catalyst bed.

In another embodiment, a supported bed reactor is disclosed comprising a reactor vessel; an ion exchange resin catalyst in the vessel to receive reactants in a downflow mode; and packing randomly distributed throughout the ion exchange resin catalyst.

In yet another embodiment, a system is disclosed for the manufacture of bisphenol A from phenol and acetone, the system comprising an acetone feed stream; an optionally jacketed phenol feed stream mixed with the acetone stream to form a feed stream mixture; a cooling apparatus to receive the feed stream mixture and a reactor connected in fluid communication with the cooling apparatus. The reactor comprises a reactor vessel having an inlet at an upper end to receive the feed stream mixture from the cooling apparatus, and an outlet at a lower end of the vessel; a supported catalyst resin bed located intermediate the inlet and the outlet. The bed comprises an ion exchange catalyst resin and an inert packing material distributed randomly throughout the resin; a temperature sensing means is in communication with the vessel, and a pressure sensing means is in communication with the vessel, a bypass stream between the inlet and the outlet; a second phenol feed stream capable of being received at the outlet; a product takeoff valve is disposed in fluid communication with the lower end of the reactor. The product takeoff valve preferably is at the same elevation as the inlet and a siphon break is located downstream of the product takeoff valve.

DETAILED DESCRIPTION

Figure 1:
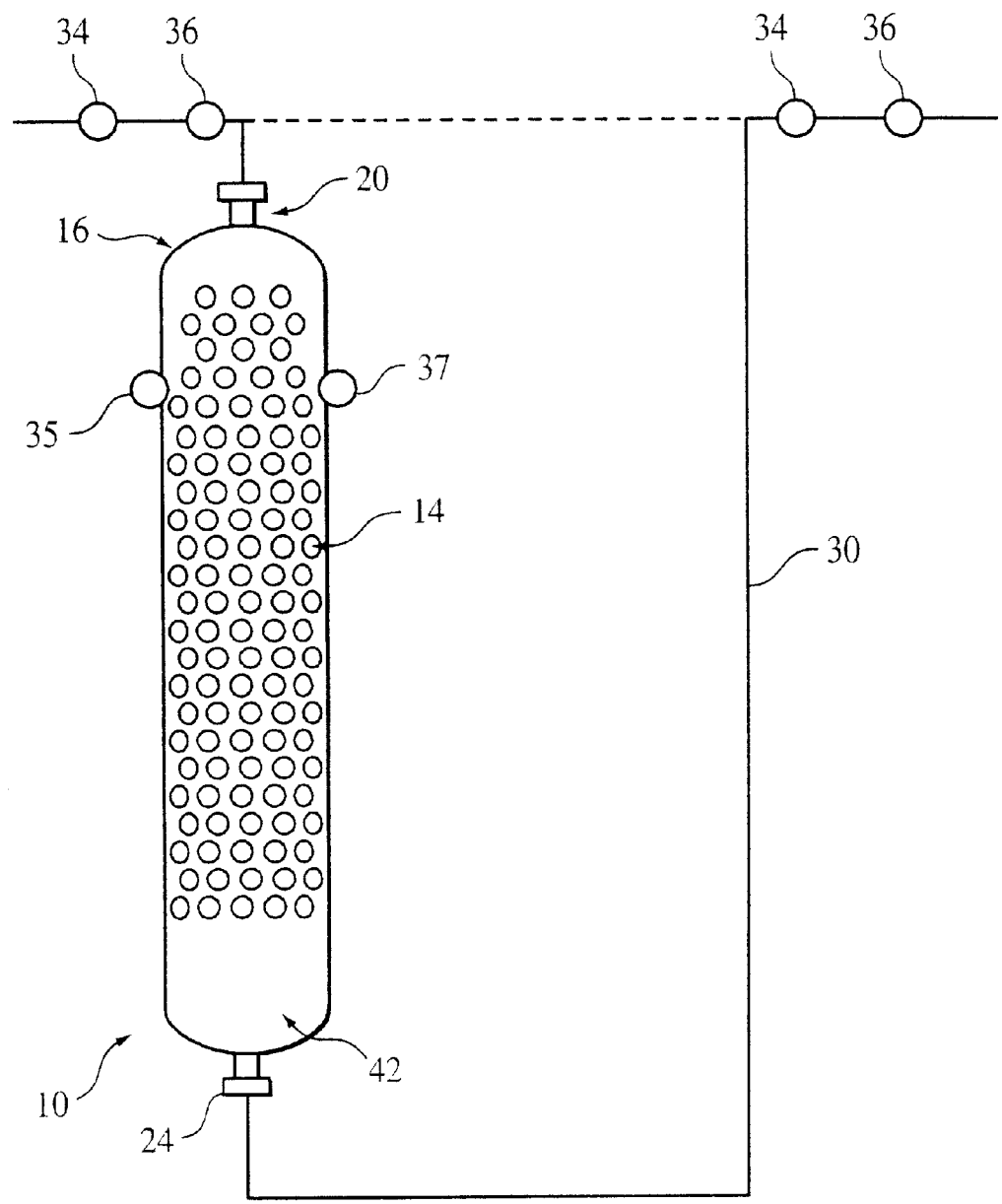
FIG. 1 is a schematic representation of a downflow chemical reactor having a supported ion exchange resin catalyst disposed therein.
Figure 2:
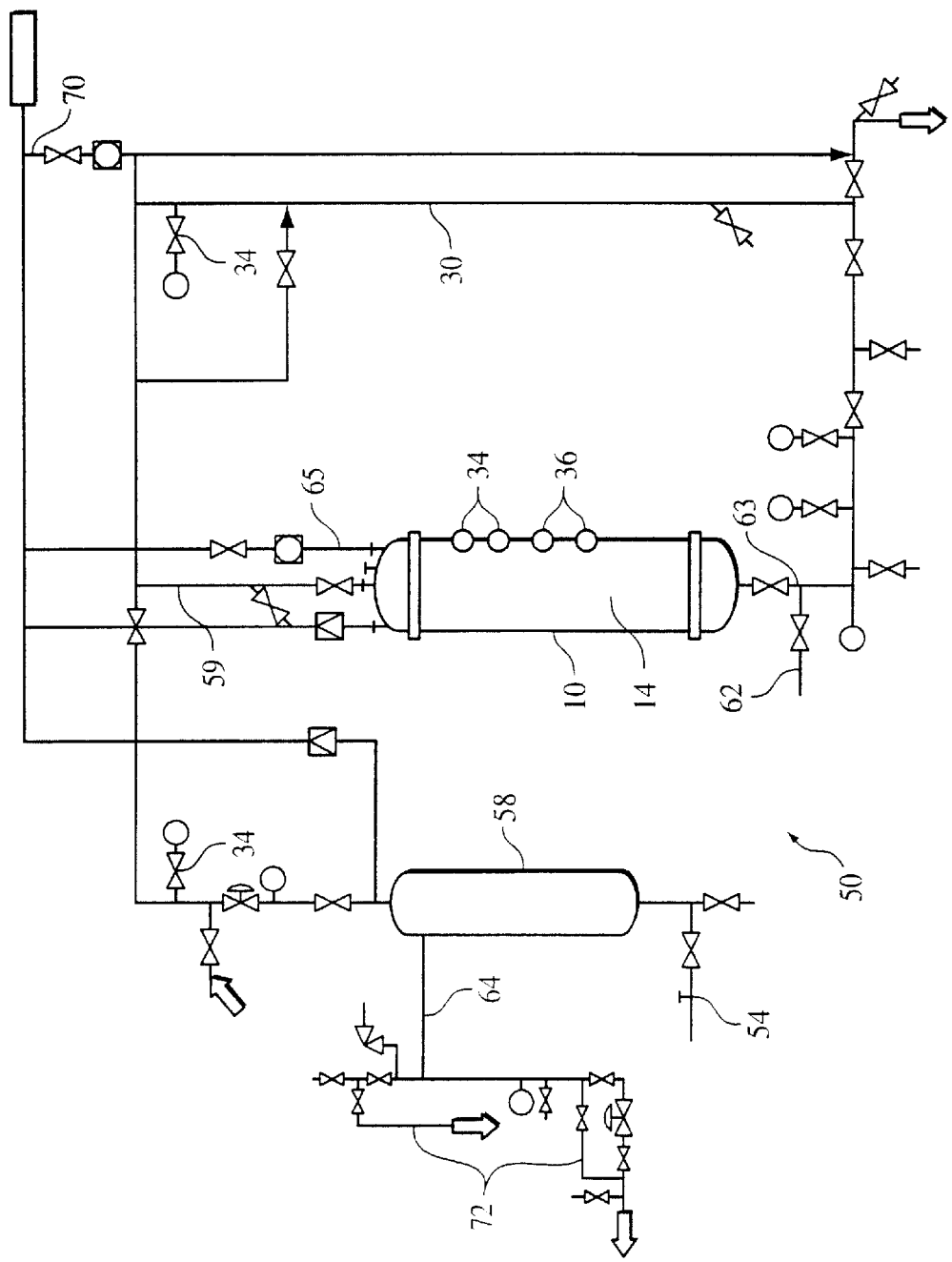
FIG. 2 is a schematic representation of a system for producing bisphenol A from the reaction of phenol and acetone with an ion exchange resin catalyst in a supported downflow catalyst bed.

An apparatus and system for producing a bisphenol and a method of use directed to the production of the bisphenol are disclosed herein with reference to FIGS. 1 and 2. Referring now to the Figures, which are exemplary embodiments and wherein the like elements are numbered alike:

FIG. 1 illustrates the type, mode and construction of the reactor.

FIG. 2 illustrates a system for use with the reactor to produce bisphenol A or other phenol isomer as desired.

The reactor includes a supported catalyst bed through which the reactants flow to catalytically produce the final bisphenol. The flow preferably used is a supported downflow mode in which reactant materials flow co-currently from a higher elevation to a lower elevation through the bed to facilitate the chemical reaction to produce the bisphenol product. Although the method is applicable to the production of any isomer of bisphenol, the preferred isomer is p,p'-bisphenol A produced by the reaction of phenol with acetone (dimethyl ketone) in the presence of an ion exchange resin catalyst which may optionally be modified by selected promoters such as, for example, mercaptan compounds, if desired. The reactor is shown in FIG. 1 at 10 and includes a bed 14 containing an ion exchange resin catalyst and randomly dispersed packing. The bed receives co-current downflow streams of the reactants. The ion exchange resin catalyst is distributed around the packing so that the catalyst is supported within the bed to minimize channeling and compressive forces, as well as to optimize the hydraulic performance of the reactor. Any type of reactor vessel used to react reactants in the presence of fixed catalyst is generally amenable to practicing this invention. However, cylindrical reactors are preferred for their simplicity.

The inlet 20 can comprise tubing, pipes, jets, or other common means for introducing reactants into the reaction zone of a reactor. Reactants are typically distributed into the reaction zone by a perforated pipe, sparging arm, or other similar or conventional means for distributing fluids. Preferably, the bottom portion of the reactor 42 is filled with aggregate. The amount of such aggregate is not critical to this invention. However, sufficient aggregate should be present to provide support to the reactor internals. This aggregate can comprise any material which is essentially inert to the reactants and products produced in the reactor. Preferably, this aggregate is comprised of silica sand, silica based gravel, ceramic balls, or a combination of these.

The reactor shell 16 has an inlet 20 at its upper end and an outlet 24 at its lower end. The interior of the shell may be vented to atmospheric pressure via a vent line (not shown), which runs normally closed. The shell 16 may also include a jacket, if desired, to accommodate a cooling stream to remove heat generated by the exothermic reaction of the reactant. Fluids that may be used for the cooling stream may include, but are not limited to, water, brines, and refrigerants.

In operation, the inlet 20 receives the reactants and distributes them to the upper surface of the resin catalyst bed. The reactants then proceed downward, through the supported bed while reacting to form the final product. The outlet 24 is in fluid communication with the bed and with a product take-off line 30 which is located at substantially the same elevation as the inlet to insure that the reactor operates in overflow mode and to insure that it remains totally liquid filled. Sensor means for measuring pressure 34 and temperature 36 may be located at the inlet and outlet, and additional sensors 35, 37 may be located at selected positions along the shell 16 to sense conditions associated with the reaction and to obtain appropriate reaction profiles. Inlet and outlet pressure transmitters are placed at the same elevation in the Development Reactor to insure that the static liquid head is equal before and after the packed supported bed for accuracy in collecting engineering and design data, showing only the delta-P which is attributable to the catalyst resin and bed support. The delta-P vs. flow relationship is exponential for the catalyst, which is compressible. Information from these sensor means is transmitted to a control unit (not shown) that adjusts selected parameters such as, for example, feed rates and the cooling stream flow to the jacket, if used.

The random arrangement of the packing in the shell provides support for the resin catalyst and minimizes compression. "Settling" of the catalyst is essential and desirable to insure complete filling of the void spaces within the catalyst bed. The packing also ensures that the cumulative compressive forces (which are the sum of the forces created by gravity and the viscous drag from the downflow of reactants) are interrupted to such a degree that high conversion, high selectivity, and long lifetime can be realized by the resin catalyst. The minimization of the compressive forces is enough that the "wall effects" of the packing elements are spread through the bed on a microscopic scale.

Generally, spherical catalyst beads fit "within" (curve within curve) the void spaces created by neighboring beads, thereby resulting in a certain void fraction through which flow can occur. However, when these spherical beads are instead located adjacent to a surface, that is, a "wall" or baffle, a probe or other flat surface, the relative geometry of those two surfaces (flat vs. curved) create a larger void fraction, and as a result, a slightly disproportionate amount of flow will occur at the "wall" than in a representative portion of the bed at large.

The bed 14 includes a plurality of discrete inert elements that are located within the shell to result in a random arrangement of surfaces that provide tortuous paths for the downward flow of the reactant materials. These discrete objects may be fabricated from any rigid, chemically inert, and thermally stable material that allows for optimum con, tact of the reactant materials as they flow through the bed while still providing support for the resin. Optimum contact is generally effected by objects having large void fractions (for example, objects that are predominantly small in volume and exhibit great surface area). The random packing elements employed may have a void fraction of 0.6 or higher such as for example 0.8. Particularly preferred elements have a void fraction of up to 0.98 or higher. Higher void fractions permit a higher loading of resin catalyst while still providing sufficient support for the bed. It is theorized that there is a correlation among the rigidity of the elements, their ability to resist deformation under load and the overall "compressibility" of the rings, and therefore the compressibility of the entire bed.

This type of inert random packing interrupts the packing structure of the spherical resin particles to provide a larger effective void fraction. The resin bed alone usually has a void fraction of about 0.36 and small increases in this is expected to result in dramatic decrease in pressure drop. Although decreased pressure drop caused by increased void fraction is less desirable than that caused by preventing compression, since the increased void fraction represents paths for "channeling" or "short circuiting", which reduces the contact time of the reactants and catalyst. Increasing the void fraction within the catalyst is less desirable than simply preventing the decrease of void fraction caused by bead deformation.

Preferably, the packing comprises metallic cascade rings, such as CASCADE MINI-RINGS® available from Koch-Glitsch, Inc., Wichita, Kans. This cascade ring has a void fraction of about 0.97. Other objects that may be utilized include typical tower packing elements such as Pall rings, Tellerette rings, Raschig rings, Berl saddles, Intalox saddles, as well as combinations of these as desired. Examples of some of these are disclosed in U.S. Pat. No. 4,041,113 and 4,086,307. In addition to better hydraulic characteristics, the preferred metallic cascade ring packing material improves the temperature differential in the reactor. This can be used to run the same inlet temperature to give a lower outlet temperature or to run at a higher inlet temperature to get more production at the same purity. Further, the temperature differential between the inlet and the outlet of the reactor packed with these elements will be less than the temperature differential between the inlet and the outlet of an unpacked reactor while conversion of reactants in each reactor is substantially equal.

Sufficient reactor packing is randomly distributed throughout the catalyst bed. In the preferred embodiment where bisphenol A is manufactured a minimum of about 25% of the catalyst bed height (measured under phenol-wet resin catalyst conditions prior to reactant entry), and most preferably at least about 30%, is occupied by randomly distributed packing. Similarly, it is preferred that the height of the packing is sufficient to remain over the height of the resin bed as the resin swells with time. This height may be about 110%, and most preferably 120% of the height of the catalyst bed. The packing should be close to the height of the resin; preferably the packing is slightly higher (up to about 20% higher) to allow for swelling of the resin over time; conceivably the packing could be shorter than the resin, because the cumulative compressive forces will be greater at the bottom of the bed than at the top.

Any method for randomly distributing the packing material may be used. The easiest and most preferred method is to simply place the packing materials into the reactor and add catalyst to the reactor to distribute within the packing void volumes.

Any commonly-known acidic ion-exchange resin catalyst may be used as the acidic catalyst, and there are no particular restrictions on this catalyst, but ordinarily, a sulfonic acid type cation-exchange resin having a degree of crosslinking of less than or equal to about 8% with less than or equal to about 6% preferred and less than or equal to about 4% most preferred. Also preferred is a crosslinking of greater than or equal to about 1% more preferred is greater than or equal to about 2%. The resin catalyst is preferably at least a partially cross-linked ion exchange resin catalyst and preferably a sulfonated aromatic resin containing some degree of divinylbenzene crosslinking and some degree of sulfonic acid functionality, for example, those disclosed in U.S. Pat. No. 5,233,096.

Acidic ion exchange resin is also used in the alkylation of phenols (U.S. Pat. No. 4,470,809). In the presence of a cation-exchange resin catalysts, alphamethyl styrene reacts with phenol to form paracumyl phenol (U.S. Pat. No. 5,185,475); and mesityl oxide reacts with phenol to form Chroman. On use, the individual particles of the resin catalyst are subject to compressive forces due to hydraulic loading; at lower levels of crosslinking the particles are less rigid and more susceptible to hydraulic deformation. The degree of crosslinking of the ion exchange resin catalyst can be up to about 4% but is more preferably up to about 2% to improve catalyst life.

It is most preferred that in the reactor system of this invention, the catalytic agents are sulfonated aromatic resins comprising hydrocarbon polymers having a plurality of pendant sulfonic acid groups. These are typically 2% or 4% divinyl benzene crosslinked. Catalysts having a 2% or lower degree of crosslinking are most preferred. Poly (styrenedivinylbenzene) copolymer, and sulfonated phenol-formaldehyde resins have utility in this regard. Sulfonated resin catalysts commercially available as "AMBERLITE A-32" and "AMBERLYST A-121" brand catalyst from Rohm and Haas Chemical Company, Inc. and "K1131" brand catalyst from Bayer Chemical Company are examples of such suitable catalysts. The exchange capacity of the acidic resin is preferably at least about 2.0 meq. H.$^+$/gram of dry resin. Ranges from 3.0 to about 5.5 meq. H.$^+$/gram of dry resin are most preferred. Optionally, co-catalysts or catalyst promoters may also be used. Either bulk or attached catalyst promoters may be employed. Many of these are well known in the art.

The instant process and reactor are particularly suitable for the production of bisphenol A (abbreviated below as BPA). If the reactor is used to produce bisphenol A then the phenol is ordinarily used in an excess amount with respect to the acetone with the molar ratio of phenol to acetone (phenol/acetone) ordinarily being greater than or equal to about 6 mols phenol to 1 mol of acetone, preferably greater than or equal to about 12 mols of phenol to 1 mol of acetone, also preferably being less than or equal to about 20 mols phenol to 1 mol acetone and, more preferably, less than or equal to about 16 mols phenol to 1 mol acetone.

The reaction of phenol and acetone is ordinarily carried out at a temperature sufficient so that the feed of the reactor remains liquid and preferably at a temperature of about 55° C. or higher. Also preferred are temperatures of less than or equal to 110° C. and more preferred less than or equal to 90° C. and most preferred about 85° C. The pressure differential across the bed when the inlet and outlet pressures are measured at equivalent elevations is preferably greater than or equal to about 0.1 p.s.i.g. and, more preferably, about 3 p.s.i.g. Also preferred are pressures of differentials of less than or equal to about 35 p.s.i.g. and, more preferably, less than or equal to about 26 p.s.i.g.

In the reaction of the above phenol and acetone, in addition to a liquid reaction mixture containing bisphenol A, usually reaction by products such as unreacted phenol unreacted acetone and water are part of the reaction mixture.

The term phenol as used throughout the specification represents phenol of the formula: as well as selected substituted phenols described in more detail below.

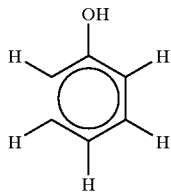

As well as bisphenol A, the bisphenol obtained by reacting phenols and ketones may have the formula below: in the formula, $R^a$ and $R^b$ are halogens or monovalent hydrocarbon groups, and they may be the same or different, p and q are integers from 0 to 4, X is $R^c$ and $R^d$ are hydrogen atoms or monovalent hydrocarbon groups or a ring structure may be formed by $R^c$ and $R^d$, and $R^e$ is a divalent hydrocarbon group. Specific examples of the bisphenol of formula above include bis(hydroxyaryl) alkanes such as: 1,1-bis(4-hydroxyphenyl)methane, 1,1-bis(4-hydroxyphenyl)ethane, 2,2-bis(4-hydroxyphenyl)propane (referred to in the following as bisphenol A), 2,2-bis(4-hydroxyphenyl)butane, 2,2-bis(4-hydroxyphenyl)octane, 1,1-bis(4-hydroxyphenyl) propane, 1,1-bis(4-hydroxyphenyl) butane, bis(4-hydroxyphenyl) phenylmethane, 2,2-bis(4-hydroxy-1-methylphenyl)propane, 1,1-bis(4-hydroxy-t-butylphenyl) propane, and 2,2-bis(4-hydroxy-3-bromophenyl)propane, and bis (hydroxyaryl)cycloalkanes such as 1,1-bis(4-hydroxyphenyl)cyclopentane and 1,1-bis (4-hydroxyphenyl)cyclohexane, 6,6'-dihydroxy-3,3,3'3'-tetramethyl-1,1'-spiro(bis) indane, 1,3-bishydroxyphenyl methane, 4,4'-dihydroxy-2,2,2-triphenylethane, 1,1'-bis(4-hydroxyphenyl)-meta-diisopropylbenzene, 1,1'-bis(4-hydroxyphenyl)-3,3,5-trimethylcyclohexane.

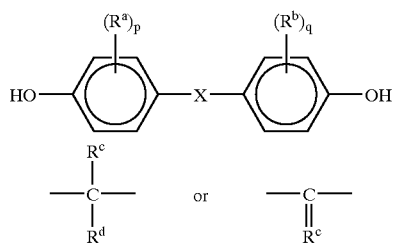

Moreover, bisphenol may be manufactured in such a manner that in the above formula, is —O—, —S—, —SO—, or SO—$_2$—, with examples of compounds that can be manufactured including bis(hydroxyaryl) ethers such as: 4,4'-dihydroxydiphenyl ether and 4,4'-dihydroxy-3,3'-dimethylphenyl ether, bis(hydroxydiaryl) sulfides such as: 4,4'-dihydroxydiphenyl sulfide and 4,4'-dihydroxy -3,3'-dimethyldiphenyl sulfide, bis (hydroxydiaryl) sulfoxides such as: 4,4'-dihydroxydiphenyl sulfoxide and 4,4'-dihydroxy-3,3'-dimethyldiphenyl sulfoxide, and bis (hydroxydiaryl) sulfones such as: 4,4'-dihydroxydiphenyl sulfone and 4,4'-dihydroxy-3,3'-dimethyldiphenyl sulfone. Among these substances, manufacturing of bisphenol A is particularly preferred.

Bisphenols such as those described above may be obtained by a commonly-known bisphenol synthesis method in which the appropriately substituted phenols and ketones are condensed in the presence of an acidic catalyst. Phenols having a structure in which there is not a bond with X in the above formula may be used. Moreover, if the above bisphenols can be obtained, one may also carry out condensation of phenols with formaldehyde, sulfonic acids, etc.

The reactants in reactor 10 react to form bisphenol (BPA when the reactants are acetone and phenol) and leave the reactor as a product stream comprising the bisphenol, unreacted reactants, optionally co-catalyst, and minor amounts of other materials.

The product stream may be fed into a separator which can be any conventional method for separating such materials. Distillation is generally the simplest and most preferred method. However, other well-known methods can be used independently or in combination with distillation to comprise this separation process.

The bisphenol product, bisphenol isomers, phenol, and a small amount of various impurities are removed from the separator as a bottoms product. This bottoms product is fed to a further separator.

Crystallization is the preferred method of bisphenol separation but any method which can be used to separate bisphenol from the mother liquor can be used, depending upon the desired degree of purity of the bisphenol product. Once separated, the dehydrated mother liquor comprising phenol and bisphenol isomers is returned to the reactor 10 as reactant.

Bisphenol separated from the mother liquor in the separator can then be sent to yet further separations and purifiers in a bisphenol recovery process. This can be particularly important where very pure product is required as where BPA is produced for use in the subsequent production of polycarbonates. Generally, such further separations can be beneficially conducted using techniques such as recrystallization.

In order to alleviate the problems associated with the compression of the ion exchange resin catalyst, the resin catalyst bed may also include layers of differently crosslinked and modified catalysts or combinations thereof. In particular, the catalyst bed may be prepared from a combination of an ion exchange resin catalyst having a higher degree of crosslinking at a lower end of the bed and an ion exchange resin catalyst having a lower degree of crosslinking at the upper end of the bed. The ion exchange resin catalyst near the upper end of the bed is preferably up to about 2% crosslinked, and the ion exchange catalyst resin on the lower end of the bed is preferably greater than about 2% crosslinked.

In operation, the shell or cylinder 16 is packed with the packing and the resin catalyst by charging it with alternating quantities of the packing and the catalyst. The catalyst can be water wet and "pre" or partially dried beads. Preferably, sand as a support and/or filter is first charged to the bottom of the shell. In a preferred embodiment, the reactor is filled to about one-fourth of its height with water and one-fourth of its height with packing elements. The column is then filled with the water wet resin and closed and phenol is run through to dehydrate the resin and shrink it into the area occupied by the elements. This procedure is repeated for the remaining column height. Additional elements are added on top of the bed for swelling during reaction. This procedure would be done with phenol if the catalyst were pre-dried.

The method for production of bisphenol A from phenol and acetone includes introducing the phenol and the acetone into the ion exchange resin catalyst bed to react the phenol and the acetone in the presence of the resin catalyst and then recovering the bisphenol A from the reaction mixture. The introduction of the phenol and the acetone is at the upper end of the bed (to facilitate the co-current downward flow of the reactants) at a rate sufficient to allow the reaction to proceed to a pre-determined yield and selectivity. The reaction of phenol and acetone is ordinarily carried out at a temperature sufficient so that the feed of the reactor remains liquid and preferably at a temperature of about 55° C. or higher. Also preferably the temperature is less than or equal to about 110° C. and preferably less than or equal to about 90° C. The introduction of the reactants is generally at a weighted hourly space velocity (WHSV) of greater than or equal to about 0.1 pound of feed per hour per pound of dry catalyst (lbs. feed/hr./lbs. catalyst) and preferably greater than or equal to about 1.0 lb. feed/hr./lbs. catalyst. Also preferred is less than or equal to about 20 lbs. feed/hr./lbs. catalyst and preferably less than or equal to about 2.0 lbs. feed/hr./lbs. catalyst. The introduction of the reactants is also generally at a flux rate of greater than or equal to about 0.1 gallon per minute per square foot of cross section of bed (gpm/ft$^2$) preferably greater than or equal to about 0.5 gpm/ft$^2$ Also preferred is an amount of less than or equal to about 2.0 gpm/ft$^2$ and most preferred is less than or equal to about 0.5 gpm/ft$^2$. The temperature of the reaction can be controlled in part by the flow of the cooling stream through the jacket to remove the heat of reaction. However, in a plug flow packed bed, radial heat transfer is low, so that the reactor functions mostly adiabatically. Packing can help improve heat transfer and thus reduce adiabaticity, improving temperature control. The temperature of the reaction can be up to about 110° C., but is preferably limited to about 85° C. During steady state operation of the reactor, the differential pressure between the inlet and the outlet 24 is greater than or equal to about 0.1 pound per square inch gauge (psig) preferably greater than or equal to about 3 psig. Also preferred is less than or equal to about 30 psig and more preferred is less than or equal to about 24 psig.

Referring now to FIG. 2, a system for the manufacture of bisphenol A from phenol and acetone is shown generally at 50. The system 50 includes a premixed feed stream 54 containing phenol, acetone and dehydrated, recycled mother liquor that is first fed to a cooling apparatus 58. The cooled feed mixture is then introduced into the reactor 10 through an inlet line 59. The mixture is then allowed to flow down through the packed catalyst bed 14 of the reactor to form the bisphenol A product. The product stream, which will include unreacted materials and some byproducts, as well as the desired bisphenol A, flows through the reactor outlet line 63. A second phenol feed stream 62 is connected to the outlet line 63 and may be used in charging the reactor. The outlet line 63 is connected to product takeoff line 30. As described above with reference to FIG. 1, the reactor 10 includes pressure sensing means 35 and temperature sensing means 37 at various positions along the shell of the reactor. A return line 64 from the cooling apparatus 58 is preferably equipped with stream tracing lines 72. (Since the materials being processed are solids at ambient temperatures, a controlled heat is added to the piping, reactor(s) and, where necessary, equipment to maintain the desired fluid temperature. This is known as "tracing" or "jacketing" on piping and equipment.) System 50 may further comprise a siphon break 70 disposed downstream of the product takeoff line 30. The reactor is vented through line 65. Either or both of the feed streams of the phenol and the acetone may include impurities recycled back from the initial reaction. The impurities, which originate from the reaction of phenol and acetone, may be isomerized in the recycle stream.

EXAMPLE 1

A reactor shell having an internal diameter of about 21 inches, a cross-sectional area of 2.377 square feet, and a height of 15 feet was charged in stage-wise fashion with quantities of packing (CASCADE MINI-RINGS®) having a bulk density of 15.3 pounds per cubic foot (lbs/ft$^3$) and 2% cross-linked wet ion exchange resin catalyst A-121 from Rohm and Haas. Between chargings, the reactor was closed and a stream of phenol containing less than 0.5% water was allowed to flow through the resin catalyst bed to dehydrate the resin catalyst. The stage-wise charging and dehydration operations were repeated until the catalyst bed was 10.5 feet in height. A total of 329.6 lbs. of packing and 3,166 lbs. of wet resin catalyst were added. The water-wet density of the resin catalyst was 45.8 wet lbs/ft$^3$ (approx. 8.5 "dry" lbs/ft$^3$), and the phenol-dehydrated density of the same resin catalyst was 24.9 "dry" lbs/ft$^3$. Upon dehydration of the resin catalyst, 592 lbs. of "dry" catalyst remained.

The differential pressure over the vertical height of the resin catalyst bed was measured at various reactor feed rates. The feed composition is similar to the values in Table III, column A. The promoter used is 3-mercaptopropionic acid at a level of about 800 ppm. Table I presented below illustrates the flow rate as measured versus the differential pressure observed across the vertical dimension of the resin catalyst bed. Average values are tabulated and it is evident that pressure increases with increasing flow rate, but this increase is mitigated by the support.

TABLE I

Differential Pressure as a Function of Flow Rate in a Supported Bed

| Flow Rate (gpm) | WHSV (Lbs Feed/Hr/Lbs Dry Catalyst) | Flux Rate (gpm/ft$^2$) | Differential Pressure ($\Delta$P) (psig) |
|---|---|---|---|
| 0.571 | 0.501 | 0.2403 | 0.41 |
| 1.141 | 1.000 | 0.4800 | 1.78 |
| 1.709 | 1.499 | 0.7192 | 5.31 |
| 2.280 | 2.000 | 0.9593 | 7.96 |
| 2.850 | 2.499 | 1.1991 | 18.6 |

EXAMPLE 2

The experimental conditions of Example 1 and the feed composition were repeated in a control experiment using the same type of resin without a packing. Table II presented below illustrates the flow rate as measured versus the differential pressure observed across the vertical dimension of the resin catalyst bed.

TABLE II

Differential Pressure as a Function of Flow Rate in an Unsupported Bed

| Flow Rate (gpm) | WHSV (Lbs Feed/Hr/Lbs Dry Catalyst) | Flux Rate (gpm/ft$^2$) | Differential Pressure ($\Delta$P) (psig) |
|---|---|---|---|
| 0.569 | 0.499 | 0.2396 | 0.37 |
| 1.140 | 1.000 | 0.4798 | 1.74 |
| 1.710 | 1.500 | 0.7194 | 11.59 |

Without the support provided by the random packing, compression of the unsupported catalyst bed under increased flow is high, and as a result, throughput, and, therefore, productivity, are severely limited. Average values are tabulated.

Figure 3:
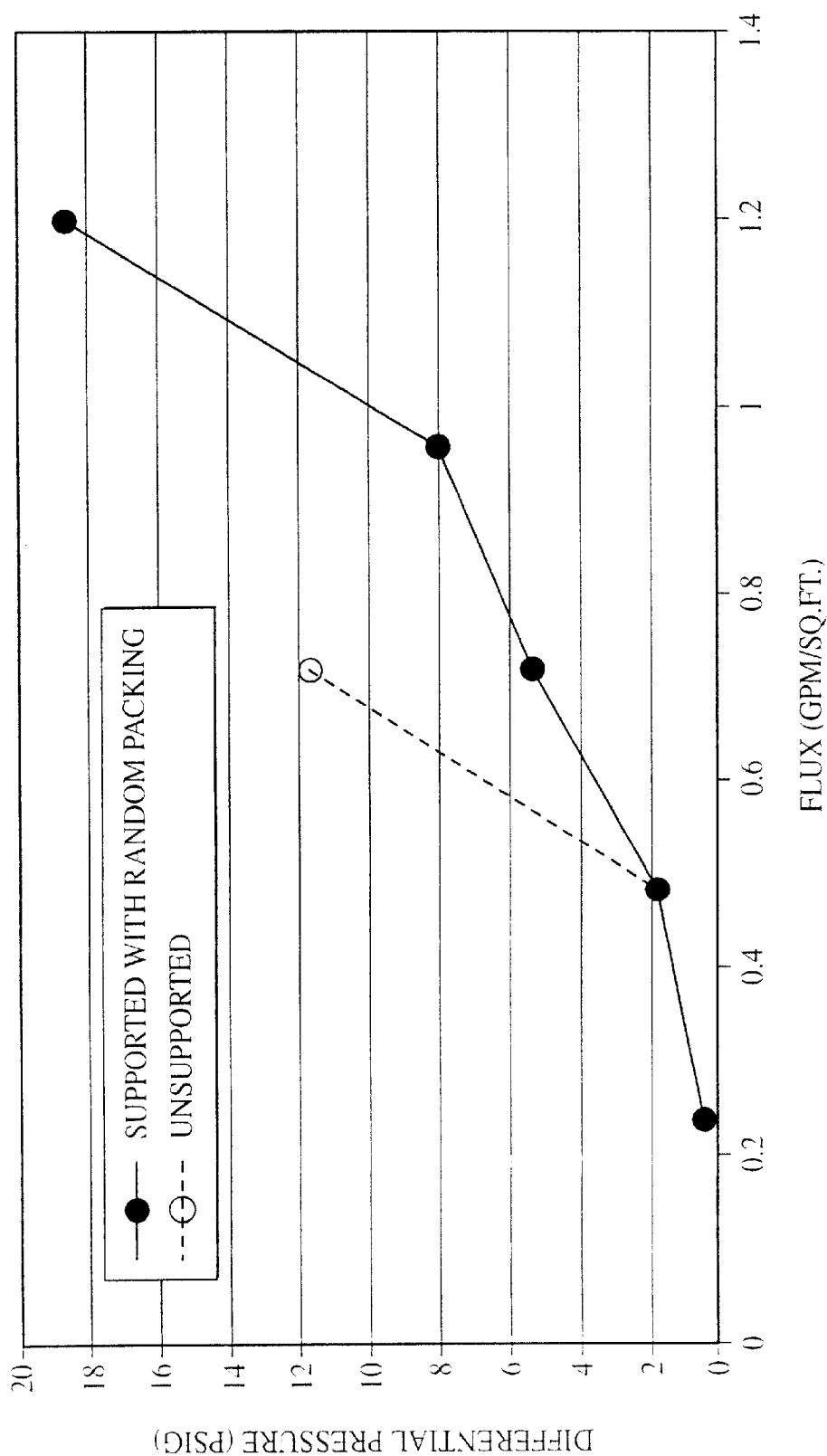
FIG. 3 is a graph showing a comparison of the increase in differential pressure through a bed of compressible resin with and without packing.

FIG. 3 compares the resin with packing of Example 1 and without packing of Example 2 under the same conditions. This figure shows that the increase in differential pressure through a bed of compressible resin is mitigated by packing for the same resin system and experimental conditions.

EXAMPLE 3

Several experiments were run at different typical process conditions and the temperature differences between the inlet and the outlet of the reactor as well as the conversion rate of the reactants were measured. These conditions and an average of a number of measurements made are reported in Table III below as follows:

TABLE III

TYPICAL EXPERIMENTAL VALUES

| | A. Rings | B. No Rings | C. Rings | D. No Rings | E. Rings | F. No Rings | G. Rings | H. No Rings |
|---|---|---|---|---|---|---|---|---|
| Flux (gpm/sq. ft.) | 0.72 | 0.72 | 0.72 | 0.72 | 0.24 | 0.24 | 0.48 | 0.48 |
| Linear Velocity (ft/min) | 0.096 | 0.096 | 0.096 | 0.096 | 0.032 | 0.032 | 0.064 | 0.064 |
| Inlet Temp (° F.) | 148.9 | 148.9 | 137.7 | 136.7 | 151.4 | 152.0 | 148.4 | 148.8 |
| Bottom Temp (° F.) | 190.0 | 191.8 | 176.3 | 185.0 | 184.5 | 194.8 | 187.3 | 192.9 |
| Exit Temp (° F.) | 182.2 | 185.6 | 172.4 | 180.5 | 175.2 | 182.4 | 178.9 | 184.8 |
| Acetone in Feed (wt %) | 4.2 | 4.3 | 4.2 | 4.4 | 3.8 | 3.9 | 3.8 | 4.1 |
| p,p-BPA in feed (wt %) | 10.8 | 10.6 | 11.6 | 10.6 | 11.1 | 10.4 | 10.9 | 10.6 |
| Acetone Conversion (%) | 95.1 | 94.6 | 94.0 | 93.0 | 98.6 | 98.4 | 97.2 | 97.0 |
| p,p Selectivity | 98.3 | 97.5 | 96.9 | 98.4 | 97.0 | 96.1 | 97.8 | 98.0 |
| Delta P (psi) | 3.7 | 5.6 | 5.3 | 11.6 | 0.4 | 0.3 | 1.8 | 1.7 |
| Production Rate (lb BPA/hr) | 136.6 | 136.9 | 128.7 | 139.8 | 41.9 | 42.7 | 84.9 | 90.2 |

Accordingly, from the above data, it can be seen that even though the conversion remains roughly equivalent for widely varying conditions, the temperature difference between the inlet and the outlet of a packed reactor with rings is less than the temperature difference between the inlet and the outlet of a reactor without packing. This is unusual in that a lower temperature differential does not favor equal conversion percentages.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A method for producing a bisphenol, comprising:
    introducing a phenol and a ketone into a reactor in a downflow mode, said reactor comprising,
    an ion exchange resin catalyst bed having packing randomly distributed in said bed, said catalyst bed optionally comprising, a catalyst promoter of a sulfur containing compound and reacting said phenol and said ketone to form a reaction mixture; and recovering said bisphenol from said reaction mixture.

2. The method of claim 1 wherein the ion exchange resin catalyst in said bed is cross-linked.

3. The method of claim 2 wherein the degree of cross-linking of said ion exchange resin catalyst is less than or equal to about 4% by weight of said resin.

4. The method of claim 3 wherein the degree of crosslinking of said resin is greater than 2% by weight.

5. The method of claim 2 wherein the degree of crosslinking of said resin is less than or equal to 2%.

6. The method of claim 5 wherein the degree of crosslinking of said ion exchange resin catalyst is about 2%.

7. The method of claim 1 wherein said ion exchange resin catalyst is a sulfonated aromatic resin.

8. The method of claim 7 wherein the attached promotor comprises a portion of the sulfonic acid groups of said sulfonated aromatic resin modified by the neutralization thereof with a sulfur containing compound.

9. The method of claim 7 wherein the bulk promotor comprises a sulfur containing compound freely dispersed in the reaction mixture.

10. The method of claim 1 wherein said packing comprises inert objects having a void volume of about 0.6 to about 0.98.

11. The method of claim 10 wherein said packing is selected from the group consisting of Pall Rings, Berl Saddles, Intalox Packing, Tellerette Packing, Hyperfill Packing, Stedman Packing, Sulzer Packing, Raschig Rings and Koch-Glitsch Cascade Mini Rings® and mixtures thereof.

12. The method of claim 10 wherein said packing comprises a major portion of Koch-Glitsch Cascade Mini Rings®.

13. The method of claim 1 wherein said promoter when present is 3-mercapto propionic acid.

14. A method for producing a bisphenol, comprising:

introducing a phenol and a ketone into a reactor system in a downflow mode, said reactor system comprising, a downflow chemical reactor, and a fixed bed ion exchange resin catalyst having packing randomly distributed therein charged in said reactor wherein said resin catalyst is a sulfonated aromatic resin having a degree of crosslinking no greater than about 2% by weight based on said resin catalyst;

reacting said ketone and said phenol in said reactor to form a reaction mixture containing said bisphenol; and recovering said bisphenol from said mixture.

* * * * *